United States Patent [19]

Burgess et al.

[11] Patent Number: 5,202,491

[45] Date of Patent: * Apr. 13, 1993

[54] PROCESS FOR THE MANUFACTURE OF DIETHYLENETRIAMINE

[75] Inventors: Lloyd M. Burgess, South Charleston, W. Va.; Charles A. Gibson, Centerville, Va.; David J. Schreck, Cross Lanes, W. Va.

[73] Assignee: Union Carbide Chemicals & Plastics Technology Corporation, Danbury, Conn.

[ * ] Notice: The portion of the term of this patent subsequent to Mar. 23, 2010 has been disclaimed.

[21] Appl. No.: 528,554

[22] Filed: May 25, 1990

Related U.S. Application Data

[63] Continuation of Ser. No. 102,929, Sep. 30, 1987, abandoned.

[51] Int. Cl.$^5$ .......................................... C07C 209/02
[52] U.S. Cl. .................................. 564/480; 544/358; 544/401; 544/402; 564/479; 564/503; 564/511; 564/512
[58] Field of Search ................ 564/479, 480, 503, 511, 564/512; 544/358, 401, 402

[56] References Cited

U.S. PATENT DOCUMENTS

| | | | |
|---|---|---|---|
| 2,479,657 | 8/1949 | Wilkes, Jr. | 260/268 |
| 3,068,290 | 12/1962 | Lichtenwalter et al. | 260/585 |
| 3,151,115 | 9/1964 | Moss et al. | 260/268 |
| 3,383,417 | 5/1968 | Lichtenwalter | 260/584 |
| 3,766,184 | 10/1973 | Johansson et al. | 260/268 SY |
| 4,400,539 | 8/1983 | Gibson et al. | 564/480 |
| 4,404,405 | 9/1983 | Winters | 564/482 |
| 4,547,591 | 10/1985 | Brennan et al. | 564/479 |
| 4,550,209 | 10/1985 | Unvert et al. | 564/479 |
| 4,560,798 | 12/1985 | Ford et al. | 564/503 |
| 4,568,746 | 2/1986 | Cowherd, III | 544/358 |
| 4,578,517 | 3/1986 | Johnson et al. | 564/479 |
| 4,609,761 | 9/1986 | Watts, Jr. et al. | 564/479 |
| 4,612,397 | 10/1986 | Renken | 564/512 |
| 4,647,701 | 3/1987 | Gibson | 564/479 |
| 4,827,037 | 5/1989 | Doumaux, Jr. | 564/479 |
| 4,918,233 | 4/1990 | Deeba et al. | 564/479 |

FOREIGN PATENT DOCUMENTS

0150558 8/1985 European Pat. Off. .
0200250 12/1986 European Pat. Off. .
0223706 6/1985 German Democratic Rep. .

OTHER PUBLICATIONS

Barnes, C. M. et al., Ind. Eng. Chem. Prod. Res. Dev. 1981, 20, 399-407.

*Primary Examiner*—Carolyn Elmore
*Assistant Examiner*—Scott C. Rand
*Attorney, Agent, or Firm*—R. M. Allen

[57] ABSTRACT

A continuously generated alkyleneamines producers composition comprising, based on 100% of the moles of the composition and exclusive of any MEA and water present, a) about 20 to about 40 mole % DETA,
b) about 15 to about 60 mole % EDA (net generated),
c) about 5 to about 18 mole % AEEA,
d) about 3 to about 25 mole % of the combination of PIP, AEP and HEP,
e) less than about 1 to about 5 mole % of one or more of TETAs and TEPAs,
f) less than about 1 mole % of other polyalkylene polyamines,
g) a DETA to AEEA mole ratio greater than about 1.35, and
h) an EDA to DETA mole ratio less than 2.60, and the process of manufacturing it which comprises feeding hydrogen, ammonia, MEA and EDA, preferably provided from a recycle stream, to a reaction zone containing a fixed bed of a reductive amination catalyst in a tubular reactor, wherein the hydrogen comprises about 1 to about 30 mole percent of the feed in the reaction zone, the mole ratio of EDA to MEA is greater than 0.25 and the mole ratio of ammonia to MEA is about 1 to about 15, the temperature of the reaction zone is about 120° C. to about 300° C., the pressure of the reaction zone is about 1800 to about 2500 psig., the conversion of MEA is about 20 to about 60 weight percent, and recovering said producers composition from the reaction zone.

3 Claims, No Drawings

PROCESS FOR THE MANUFACTURE OF DIETHYLENETRIAMINE

This application is a continuation of U.S. application Ser. No. 07/102,929, filed Sep. 30, 1987, now abandoned.

RELATED APPLICATIONS

The following commonly assigned applications: Ser. No. 07/528,879, filed May 25, 1990, now pending, which is a continuation of Ser. No. 07/102,930, filed Sep. 30, 1987, now abandoned; Ser. No. 07/528,555, filed May 25, 1990, now pending, which is a continuation of Ser. No. 07/102,927, filed Sep. 30, 1987, now abandoned; Ser. No. 07/576,987, filed Sep. 4, 1990, now U.S. Pat. No. 5,068,330, which is a division of Ser. No. 07/102,928, filed Sep. 30, 1987, now U.S. Pat. No. 4,977,266; Ser. No. 07/576,988, filed Sep. 4, 1990, now U.S. Pat. No. 5,068,329, which is a division of Ser. No. 07/102,931, filed Sep. 30, 1987, now U.S. Pat. No. 4,973,692.

BRIEF DESCRIPTION OF THE INVENTION

The invention concerns an alkyleneamines producers composition rich in diethylenetriamine (DETA), and the method for forming it.

BACKGROUND TO THE INVENTION

A significant portion of the ethylenediamine (EDA) made commercially is by the continuous reaction of monoethanolamine (MEA) and ammonia in the presence of hydrogen over a fixed bed reductive amination catalyst. The reaction unavoidably generates a variety of polyalkylene polyamines as well. Illustrative of many of them are the following:

AEEA-N-(2-aminoethyl)ethanolamine
HEP-N-(2-hydroxyethyl)piperazine
DETA-Diethylenetriamine
AEP-N-(2-aminoethyl)piperazine
TETA-Triethylenetetramine
TEPA-Tetraethylenepentamine
PEHA-Pentaethylenehexamine
  TETA Isomers:
NTEA-Nitrilotrisethylamine
TETA-Triethylenetetramine
DiAEP-Diaminoethylpiperazine
PEEDA-Piperazinoethylethylenediamine
  TEPA Isomers:
AETETA-4-Aminoethyltriethylenetetramine
TEPA-Tetraethylenepentamine
AEPEEDA-Aminoethylpiperazinoethylethylenediamine
PEDETA-Piperazinoethyldiethylenetriamine Gibson, et al., U.S. Pat. No. 4,400,539, patented Aug. 23, 1983, describes such a process for the manufacture of ethylenediamine. The patent describes a continuous process involving the reductive amination of MEA. A further elaboration of the process of the Gibson, et al. patent is described in Winters, U.S. Pat. No. 4,404,405, patented Sep. 13, 1983. The Gibson, et al. and Winters patents characterize the relative commercial values attributed to ethylenediamine and piperazine. The direction which the art has been moving in recent years has been away from piperazine towards a more favored product, EDA. These patents provide ample descriptions of recovery systems for the separations and recovery of the various products of the reaction.

Another valuable product of the reaction is DETA. The market demand for DETA has been progressively increasing in recent years. It is a desirable co-product with EDA.

The compositions generated by that reaction are dependent upon a number of factors such as the selection of catalyst for carrying out the reaction, the ratio of reactants, the temperature, the pressure, reactant flow velocity through the catalyst zone, the shape and form of the catalyst, the presence and absence of other reactants such as water, and the like considerations. There are a wide variety of reductive amination catalysts for this reaction. Typically, they are viewed as hydrogenation catalysts. The most prevalent of them utilize nickel as an important ingredient. Raney nickel has for years been viewed as a good hydrogenation catalyst. In recent years, nickel in combination with other metals has grown to be a favored catalyst for effecting the reductive amination reaction.

An excellent survey of that process and the alkyleneamines compositions generated thereby can be found in Barnes et al., *Ind. Eng. Chem. Prod. Res. Dev.* 1981, 20, 399–407. Table II, at page 402, lists a variety of patent examples and the disclosed products of MEA ammonolysis.

According to Barnes et al.

"The apparently simple reaction of $NH_3$ and MEA to yield EDA is deceptive, for several catalytic steps are involved, and a number of side reactions occur."

The variety of products generated by that reaction reflects the complexity of the chemistry involved.

Lichtenberger, et al., U.S. Pat. No. 3,068,290, patented Dec. 11, 1962, referred to in Table II of Barnes et al., supra, describes the batch manufacture of EDA by the reaction of MEA and ammonia in the absence of hydrogen in the presence of Raney nickel in an autoclave, and depicts in Example III, the following composition, exclusive of MEA and water:

| Product | Weight (g.) | Moles | Mole % |
| --- | --- | --- | --- |
| EDA | 260 | 4.48 | 56 |
| PIP | 70 | 0.81 | 10 |
| DETA | 103 | 1.0 | 13 |
| AEEA | 138 | 1.33 | 17 |
| TETAS + VARIOUS AMINES | 48 | .33 | 4 |

Because the various amines are unknown compositions, they were treated as TETAS for the purposes of this characterization.

Johansson, et al., U.S. Pat. No. 3,766,184, patented Oct. 16, 1973, criticizes the commercial applicability of the catalyst, and hence the process, of Lichtenberger, et al., see the discussion at col. 2, lines 18 to col. 3, line 5. However, a point not raised by Johansson, et al., is the absence of hydrogen in the process of Lichtenberger, et al. The absence of hydrogen makes the process of Example III of Lichtenberger, et al. not readily reproducible, if ever reproducible, in a continuous process.

It is fairly well appreciated in the reductive amination art that the reductive amination catalyst must be first reduced before effecting the reaction, and then continuously reduced during the course of the reaction in order to keep the catalyst active and functioning. The degree of this reduction will determine the catalyst's productivity and selectivity to products. In the case of Lichtenberger, et al.'s Example III, the Raney nickel had to have been reduced with hydrogen prior to use. It is that level of hydrogenation that will sustain the reaction. As the level of the catalyst's surface becomes depleted of bound hydrogen, the catalyst's activity is reduced and its composition is changed. Eventually the catalyst will become depleted of its bound hydrogen, and when that occurs, the reaction terminates. In the course of the reaction, the composition of the reaction product changes from what it was at the start of the reaction. What is found in the reactor is a composite composition that changes over the course of the limited life of the catalyst. Needless to say that this is not an acceptable parameter of a commercial process.

Cowherd, U.S. Pat. No. 4,568,746, patented Feb. 4, 1986, describes a process for the manufacture of DETA by the selfcondensation of EDA or the coreaction of EDA and MEA. Another product of the reaction is ammonia. Ammonia is not provided in the feed to the reaction. Important process features cited in that patent is the use of a nickel, cobalt or rhodium catalyst, and a temperature between about 170° C. to about 210° C. with an EDA conversion less than about 35%. The only illustrations using MEA employed EDA/MEA mole ratios of 6:1 and 1:1.

As indicated above, there is a significant market demand for DETA. It would be desirable to be able to satisfy that demand from a cost standpoint by modifying slightly the commercial processes directed to the manufacture of EDA from the reaction of MEA and ammonia, to the production of EDA and DETA as major products.

It would be desirable to have continuously produced compositions generated by the reaction of MEA and ammonia over a fixed bed of a reductive amination catalyst under commercial conditions that are rich in EDA and DETA, and that are not disproportionately high in PIP, other cyclics and higher polyalkylene polyamines such as the TETAs, TEPAs and the higher ethoxylates and alkyleneamines thereof.

It would be very beneficial to have a process which increases one's ability to generate the manufacture of desirable products such as EDA and DETA without generating large amounts of cyclic alkylenepolyamine products. In addition, it is also desirable to have a process which emphasizes the manufacture of DETA over a reductive amination catalyst, without the need of avoiding the use of ammonia as exemplified in Cowherd, and thus co-generating the production of EDA. These features are provided by the invention.

THE INVENTION

The invention is directed to a continuously generated alkyleneamines producers composition comprising, based on 100% of the moles of the composition and exclusive of any MEA and water present,
a) about 20 to about 40 mole % DETA,
b) about 15 to about 60 mole % EDA (net generated), preferably about 25 to about 55 mole % EDA (net generated),
c) about 5 to about 18 mole % AEEA, preferably about 5 to about 13 mole % AEEA, and most preferably about 5 to about 10 mole % AEEA,
d) about 3 to about 25 mole % of the combination of PIP, AEP and HEP, preferably about 5 to about 20 mole % of the combination of PIP, AEP and HEP,
e) less than about 1 to about 5 mole % of one or more of TETAs and TEPAs,
f) less than about 1 mole % of other polyalkylene polyamines,
g) a DETA to AEEA mole ratio greater than about 1.35, and
h) an EDA to DETA mole ratio less than 2.60.

The invention is also directed to the process of manufacturing the alkyleneamines producers composition comprising, based on 100% of the moles of the composition,
a) about 20 to about 40 mole % DETA,
b) about 15 to about 60 mole % EDA (net generated), preferably about 25 to about 55 mole % EDA (net generated),
c) about 5 to about 18 mole % AEEA, preferably about 5 to about 13 mole % AEEA, and most preferably about 5 to about 10 mole % AEEA,
d) about 3 to about 25 mole % of the combination of PIP, AEP and HEP, preferably about 5 to about 20 mole % of the combination of PIP, AEP and HEP,
e) less than about 1 to about 5 mole % of one or more of TETAs and TEPAs,
f) less than about 1 mole % of other polyalkylene polyamines,
g) a DETA to AEEA mole ratio greater than about 1.35, and
h) an EDA to DETa mole ratio less than 2.60, which comprises feeding hydrogen, ammonia, MEA and EDA, preferably provided from a recycle stream, to a reaction zone containing a fixed bed of a reductive amination catalyst in a tubular reactor, wherein the hydrogen comprises about 1 to about 30 mole percent of the feed in the reaction zone, the mole ratio of EDA to MEA is greater than 0.25 and the mole ratio of ammonia to MEA is about 1 to about 15, the temperature of the reaction zone is about 120° C. to about 300° C., the pressure of the reaction zone is about 1800 to about 2500 psig., the conversion of MEA is about 20 to about 60 weight percent, and recovering said producers composition from the reaction zone.

DETAILS OF THE INVENTION

DETA is a very useful commercial product for a variety of applications. There is lacking a commercial process for the manufacture of enhanced quantities of DETA, especially as a significant product of reaction. There is a need for the ability to commercially generate larger production quantities of DETA and that is the direction of this invention.

It is an objective of this invention to effect a reaction of MEA in the presence of hydrogen, ammonia and EDA to produce in a continuous manner a reaction product mixture, termed herein an "alkyleneamines producers composition," in which DETA is a principal product of the reaction. It is a particular objective of this invention to effect the continuous reaction of MEA with hydrogen and EDA over a solid reductive amination catalyst in a tubular reactor to produce EDA and DETA as the principal products of the reaction. It is also an objective of this invention to effect the reaction of MEA, EDA, ammonia and hydrogen over a fixed bed of a solid reductive amination catalyst to produce EDA as another principal product of the reaction jointly with DETA as a secondary, but also a principal product, of the reaction. It is another objective of the invention to produce in a continuous manner, an alkyleneamines producers composition rich in the combination of EDA and DETA using a recycle stream comprising EDA mixed with water, particularly a water-EDA azeotropic mixture and water-EDA-PIP mixtures such as those derived from the EDA distillation column(s) in the separations system downstream of the reaction.

The alkyleneamines producer compositions of the invention can be subjected to conventional separations techniques for recovering the individual components of the compositions. Illustrations of such techniques can be found in Gibson, et al., Winters and Moss, et al., supra.

In the foregoing description of the compositions of the invention, the TETAs and the TEPAs include the variety of hydroxyethyl components generated in the reactions herein set forth, such as hydroxyethyl DETA and hydroxyethyl TETAs. Thus for the purpose of this invention, the TETAs and TEPAs embraced by the specification and the claims include this variety of hydroxyethyl components.

The process of this invention is distinctive insofar as it achieves the generation of high concentrations of DETA in a manner which can be suitably employed in a commercial process, particularly a continuous process, for the manufacture of alkyleneamines. In particular, the process of this invention allows the production of DETA in relatively high yields while at the same time producing EDA also in relatively high yields. The amounts of EDA set forth in the composition of the invention is the net generated EDA; over and above the amount fed to the reaction. It can be termed the net gain in EDA.

The process of the invention allows one to utilize a contaminated stream of EDA taken from the reflux portion of an EDA distillation column, a stream that at best is difficult to clean up to recover EDA values. The invention allows the use of a recycle stream containing PIP yet there is no apparent net increase of PIP in the reaction product by reason of its presence.

As indicated above, the pressure for carrying out the process for this invention is about 1,800 psig. (12411 kPa.) to about 2,500 psig. (17238 kPa.), however, it is preferred that the pressure used in practicing the process is less than about 2,300 psig. (15859 kPa.).

The process is typically carried out at a temperature between about 120° C. (248° F.) and about 300° C. (572° F.), preferably from about 150° C. (302° F.) and about 250° C. (482° F.).

The process of this invention is effected by feeding to a tubular reactor a stream of the reactant mixture comprising EDA, MEA and ammonia in the mole ratio of (1) EDA to MEA of at least 0.25,
   (i) preferably at least 0.30,
   (ii) typically not greater than about 0.5,
   (iii) preferably, not greater than 0.5,
(2) ammonia to MEA of about 1 to about 15,
   (i) preferably about 5 to about 10, where hydrogen comprises about 1 to about 30 mole percent of the feed, to the reaction zone therein containing a fixed bed of the reductive amination catalyst. Water may be provided in the feed up to 20 weight % of the weight of the MEA. The reaction zone is defined as a zone in the reactor containing the catalyst where the reaction is initiated, that is, where there is a condensation reaction going on between EDA, MEA and ammonia. The reaction zone ends when the principal reactions between EDA, MEA and ammonia ceases or the feed stream is out of contact with the catalyst, whichever is the later to occur in time.

The feed stream may be liquid, supercritical fluid or gaseous. The reaction product stream taken from the reaction zone may be liquid, supercritical fluid or gaseous. It is not necessary that the feed stream and the reaction product stream be in the same physical state. For example, the reactant stream may be gaseous and the reaction product stream liquid, and vice versa.

The tubular reactor design is not narrowly critical. The feed thereto may be upflowing or downflowing. Tubular reactors which provide the most favorable plug flow conditions are favored. The tubular reactor may be straight or curved. Design features in the reactor which optimize plug flow in the reactor may be employed. The process of this invention benefits significantly from good plug flow of the reactants and the reaction products through the reactor.

The reactant feed to the reactor is preferably in accordance with the process characterized in Gibson, et al., supra. A slight modification to that description is all that is required to effect the process of this invention. That modification involves the addition of EDA to the feed to the amination reactor 36. There are a number of way that this can be done. EDA can be supplied from storage to the reactant feed stream or EDA can be recycled from an effluent of still 52. The effluent can be a pure stream of EDA take from line 51 or a water containing mixture taken as a sidestream from the side of still 52. The sidestream can be derived from the EDA-water reflux in the still used to facilitate EDA separation. That mixture typically contains about 5 to about 30 weight percent water, about 70 to about 95 weight percent EDA and about 0 to about 10 weight percent PIP, preferably at least 0.01 to about 10 weight percent PIP, basis 100 weight percent of the mixture.

An advantage of the composition and process of the invention is that the composition has no more PIP and other cyclic amines than would the same composition made without the addition of EDA and PIP, when PIP is added. The process generates no increase in ammonia, which Cowherd, supra, indicates is generated with his process of selfcondensing EDA.

The catalysts which may be employed in the practice of this invention are those which have previously been employed for the condensation reaction of an alkanolamine and ammonia. There is an abundance of art which cite the type of catalysts which may be employed in the practice of this invention. Illustrative art which depict catalysts suitable for use in the practice of this invention are the following:

| | |
|---|---|
| U.S. 4,560,798 | patented December 24, 1985 |
| U.S. 4,463,193 | patented July 31, 1984 |
| U.S. 4,362,886 | patented December 7, 1982 |
| U.S. 4,316,841 | patented February 23, 1982 |
| U.S. 4,316,840 | patented February 23, 1982 |
| U.S. 4,314,083 | patented February 2, 1982 |
| U.S. 4,503,253 | patented March 5, 1985 |
| U.S. 4,578,517 | patented March 25, 1986 |
| U.S. 4,521,600 | patented June 4, 1985 |
| U.S. 4,394,524 | patented July 19, 1983 |
| U.S. 4,555,582 | patented November 26, 1985 |
| U.S. 4,584,406 | patented April 22, 1986 |
| U.S. 4,588,842 | patented May 13, 1986 |
| U.S. 4,550,209 | patented October 29, 1985 |
| U.S. 4,552,961 | patented November 12, 1985 |
| U.S. 4,588,842 | patented May 13, 1986 |
| Japanese Patent Appl. No. 262713/85 Laid-open No. 130260/86 | filed November 25, 1985 |
| U.S. 4,123,462 | patented October 31, 1978 |
| U.S. 4,111,840 | patented September 5, 1978 |

| | -continued | |
|---|---|---|
| EPC SN 83113181.8 | filed December 28, 1983 | |
| U.S. 4,568,746 | patented February 4, 1986 | |
| U.S. 4,552,961 | patented November 12, 1985 | |
| U.S. 4,647,701 | patented March 3, 1987 | |
| U.S. 4,625,030 | patented November 25, 1986 | |

The reductive amination catalyst is a classical hydrogenation catalyst. As is the case with the preponderance of the hydrogenation catalysts they typically contain such metals as nickel, rhodium, rhenium, zinc, palladium, platinum, and the like. A particularly desirable reductive amination catalyst is based on the presence at the catalyst's surfaces of nickel.

Of particular interest as a reductive amination catalyst is a potentiated catalyst comprising nickel on various support materials including a-alumina, silica, silica-alumina, kieselguhr, diatomaceous earth and silica-titania which are active and selective in the conversion of various alkane derivatives to amine products. The potentiation of the catalysts is provided by the incorporation with the nickel of a potentiating amount of a metal component of one or more of iridium and platinum. Iridium is the preferred potentiating agent.

These potentiated catalysts comprising nickel impregnated or coated together with a potentiating agent on a support material selected from alumina, silica, silica-alumina, kieselguhr, diatomaceous earth, and silica-titania, wherein the mole ratio of the nickel to total potentiating agent is in the range of from 1:1 or 2:1 to about 30:1 and the total nickel metal and potentiating agent present is in the range of about 1 to 30%, say about 3-30% by weight of the support.

The potentiated nickel catalyst are made by (i) impregnating a mixture of metals comprising the potentiating agent iridium and nickel on a support material selected from the group consisting of alumina, silica, silica-alumina, kieselguhr, diatomaceous earth and silica-titania; and (ii) activating said catalyst by heating the catalyst in the presence of hydrogen at a temperature in the range of about 200°-600° C. for a period of about 45 minutes to about 4 hours.

The support materials for the potentiated catalysts which have been found to produce the most active and selective amination catalysts are those supports which are composed of silica, silica-alumina, alumina, silica-titania, kieselguhr or diatomaceous earth. Most of these support materials are well-known in the art and are commercially available.

Support materials are not equivalent in their ability to form active potentiated nickel catalysts. For example, carbon-supported, potentiated nickel catalysts using CXC carbon from National Carbon Company, even with large surface areas, have not shown appreciable catalytic activity in amination reactions.

Even the aforementioned support materials which have yielded active potentiated nickel catalysts are not equivalent. Those supports which form more active catalysts yield optimum amination conversions at less severe reaction conditions, e.g., lower reaction temperatures. Therefore, although all supports tested within the group indicated above show some catalytic activity in the amination reaction, some supports within a general type have not been considered as having strong commercial promise because more extreme reaction conditions, such as higher reaction temperatures, must be used to obtain satisfactory conversions.

The actual effectiveness of a material as a support in a potentiated nickel catalyst is generally not predictable in advance. However, among the general types of supports indicated above that have been found active, there appears to be some relationship between catalytic activity and the amount of the surface area of the particular support materials.

Specific examples of some of the more active support materials for the potentiated nickel catalysts are listed in the table below:

TABLE

| Support | General Type | Surface Area $m^2/gm$ |
|---|---|---|
| Girdler T869 | Silica-alumina | about 60 |
| Girdler T1571 | Silica-alumina | about 150 |
| Girdler T372 | alpha-alumina | about 40 |
| Girdler T373 | Silica-alumina | 2-3 |
| Girdler K302 | Silica-alumina | about 250 |
| Girdler T2085 | Silica-alumina | about 113 |
| Girdler K10 | Silica-alumina | about 268 |
| Girdler T2045 | Kieselguhr | |
| Norton LA 4102 | alpha-alumina | 1 |
| Johns-Manville Type III | Diatomaceous silica | 10-15 |
| Grace 980-13 | Silica alumina | about 375 |
| Grace 980-25 | Silica alumina | about 375 |
| Laboratory | Silica titania $(SiO_2/TiO_2$ Mole Ratio 9:1 to 1:9) | about 75-115 |

In the amination reactions of the present invention, supports having a surface area of 1 $m^2$/gm or greater are preferred.

The support materials which may be used in making the catalyst may be of any convenient shape or size. The shape of the support usually will depend upon the shape required in the particular apparatus used to perform the catalyst conversion reaction. Catalysts can be made on support materials in the form of powders, spherical pellets and extruded strips. Impregnated spherical pellets ranging in diameter from ⅛ inch to 3/16 inch and extruded strips of a cylindrical-type shape ranging from 1/32 inch to ¼ inch in length are typical of those which can be used as supports.

The particular method of impregnating or coating the nickel and potentiating agent onto the support material has an insignificant effect on the activity or selectivity of the final catalyst in amination processes; however, impregnated catalysts generally perform better than coated catalysts. The amount of metal provided on the support material and the nature of the support itself can affect or vary the catalytic activity and/or selectivity.

One technique for impregnating the nickel and potentiating agent onto the support is to use a solution of salts of the metals as a vehicle. Various organic and inorganic nickel and potentiating agent salts may be used in impregnation solutions. Examples of suitable nickel-containing salts are anhydrous and hydrated nickelous nitrate hydrate: [Ni(—$NO_3)_2 6H_2O$] and nickel acetonyl acetate [Ni($C_5H_7O_2)_2$]. Suitable potentiating agent salts for use in the impregnating solution are platinum (II) chloride, platinum II acetylacetonate, iridium (III) chloride, iridium (III) acetylacetonate. In some cases, it is advantageous to heat the solvent liquid to bring the metal salts into solution.

The salt solution should be prepared by considering two factors. The first concerns the amount of total metal desired to be impregnated on a specific quantity of support. The second factor concerns the relative atom ratio of nickel to potentiating agent. Both factors have been found to affect the final properties of the catalyst.

Some active catalysts have been found to be those in which the nickel to potentiating agent atom ratio is between 1:1 and 30:1. In most cases, maximum activity occurs with this ratio being between about 5:1 and 20:1. In preparing the catalyst, this atom ratio is obtained by predetermining the corresponding relative proportions of the metal salts to be present in the impregnation solution.

The total metal to be impregnated onto the support also has an effect on the activity of the catalyst. The potentiated nickel catalysts typically contain a total nickel plus potentiating agent metal content in the range of about 1 or 3 to 30%, e.g., about 5 to 20%, by weight of the support material.

Where relatively large amounts of metal are to be impregnated on supports, a single impregnation step may not be sufficient. Although an impregnation solution may be prepared with the minimum amount of solvent required to dissolve the metal salts, the total amount of the impregnation solution may be greater than that which the support material can absorb.

In such case, a portion of the impregnation solution less than the maximum absorption amount is used to initially contact the support material. After contacting, the support material is dried and then contacted with an additional amount of impregnation solution. The sequential steps of contacting with solution and drying are continued until all of the impregnation solution is used. A typical drying step can comprise heating the impregnated support to a temperature of 120° C. for several hours. Evacuation drying may also be used, where the support is cooled under reduced pressure.

It is also advantageous to dry the support material prior to impregnation in order to ensure that the support will take up as much of the solution as possible. This pre-drying step also enables the metal to permeate more deeply into the support during impregnation. The penetration of the metal into the support may be further increased by techniques known to those skilled in the art such as by increasing the time the support is in contact with the solution. Other impregnation techniques are well known in the art and may be utilized in the present invention.

Another technique which can be used is often characterized as a "sugar coating" technique where the metal is predominantly present on the outer surface of the support material. The sugar coating technique differs from the impregnation process described above by the addition of a precipitant at the time the impregnating salt solution is in contact with the support material. The precipitant converts the metal salt solution into a slurry. This impregnating vehicle reduces the penetration of the salts beyond the surface of the support material. The slurry in contact with the support material is then evaporated to dryness leaving the metal adhering predominantly to the support surface.

After the support material is impregnated with the desired amount of nickel and potentiating agent, it is completely dried and then activated by a reduction step.

The drying step to be used is any technique which sufficiently evaporates the volatile constituents of the impregnating solution. The drying step may comprise heating the catalyst to a temperature of about 120° C. The drying may be done under an inert atmosphere such as nitrogen, and the catalyst may be cooled under reduced pressure.

The catalyst is then activated by a suitable step wherein the impregnated metal is converted into a catalytically-active form. This activation may include alloy formation, proper phase orientation of the metals and/or an adjustment in the oxidation level of the metals. An activation step may include a typical reduction process.

The preferred activation of the catalyst is to contact it with a hydrogen atmosphere which is fed over the catalyst at an elevated temperature in the order of about 200° to about 600° C. for periods of from about 45 minutes to about 4 hours. The specific conditions for reduction are dependent upon the particular catalyst composition being activated.

Prior to the activation step, the catalyst may be optionally calcined. In a preferred calcining step, the catalyst is heated to temperatures in the range of about 300° to 550° C. for one minute to about 3 hours or more. It is preferred that the calcining be carried out in air. The drying step referred to above may be replaced by the calcining step or activating step.

The potentiated nickel catalysts include catalysts which contain various other metals in admixture with the nickel and potentiating agent which do not detrimentally affect catalytic properties. These additional metals, in certain amination processes, may actually improve selectivity and activity of the basic potentiated nickel catalyst. Certain of these metals may extend the activity life and other physical properties of the catalyst. Examples of additional metal components include lanthanum, boron, magnesium, lithium, sodium, potassium, rubidium, cesium, cerium, iron, ruthenium, copper, silver, zinc, cobalt, palladium, titanium, manganese, rhodium, and rhenium. In order to prepare such catalysts, salts of these additional metals are added in suitable amounts to the impregnation solution containing the nickel and potentiating agent. The amount of such additional metal components, based on nickel and expressed as an atomic ratio, is about 0.001:1 to 1:1, frequently about 0.01:1 to 0.5:1. Particularly preferred catalysts comprise nickel, iridium and rhenium. In these catalysts, the rhenium is generally provided in an atomic ratio of iridium of about 10:1 to 1:10.

In the case of the nickel-rhenium catalysts, the preferred mole ratio of the nickel to the rhenium is the range of from 2:1 to about 30:1 and the total nickel and rhenium metal present is in the range of 3 to 30 percent by weight of the support. Such catalysts can be prepared by the methods taught in U.S. Pat. Nos. 4,111,840 and 4,123,462, the pertinent parts of which are incorporated herein by reference. Basically, such catalysts are solid catalysts wherein the nickel and rhenium metals are supported on certain catalyst support materials.

The nickel-rhenium catalyst can contain various other metals in admixture with the nickel and rhenium which do not detrimentally affect the catalytic properties of catalysts containing nickel and rhenium as the only impregnated metals. These additional metals can actually improve selectivity and activity of the basic Ni-Re catalyst. Certain of these metals can extend the activity life and other physical properties of the Ni-Re catalyst. Examples of catalysts containing additional metal components include Ni-Re-La, Ni-Re-Ca, Ni-Re-Mg, Ni-Re-Sr, Ni-Re-Li, Ni-Re-K, Ni-Re-Ba, Ni-Re-Ce, Ni-Re-W, Ni-Re-Fe, Ni-Re-Ru, Ni-Re-Cu, Ni-Re-Ag, Ni-Re-Zn, Ni-Re-Co, Ni-Re-U, Ni-Re-Ti, Ni-Re-B and Ni-Re-Mn.

The amount of Ni-Re catalyst present in the process depends on many variables including the relative proportions of the reactants, reaction conditions and the degree of conversion and selectivity desired. Moreover, the amount of catalyst will depend also on the nature of the catalyst itself, e.g., its metal loading and activity and age. The catalyst must be present in the reaction zone in sufficient catalytic amount to enable the desired reaction to occur. This is also true for any of the catalysts useful in the invention process.

Other preferred reduction amination catalysts are catalyst composed of rhenium, nickel and boron impregnated on a support material selected from the group consisting of aluminas (e.g., alpha), silicas, silica-aluminas, kieselguhrs or diatomaceous earths and silica-titanias, wherein the ratio of nickel to boron to rhenium is in the range of from about 2:2:1 to about 30:30:1 and the total nickel, boron and rhenium present is in the range of about 3 to about 30 percent by weight of the support material.

The most preferred mode of the catalyst is a reductive amination catalyst which has a silica support marketed under the mark T-869 ® by United Catalyst Incorporated. The best mode of the catalyst is obtained from the United Catalyst Incorporated. It is believed that the catalyst is prepared by impregnating the T-869 ® catalyst support with an aqueous solution containing nickel nitrate, ammonium perrhenate and boric acid in a metal composition of 66 percent of nickel, 19.6 percent of rhenium and 14.4 percent of boron. Following the impregnation, it is calcined at 330° C. for 2.5 hours. Then it is impregnated a second time with the same solution and calcined again under the same conditions for the same length of time. Thereafter, it is impregnated a third time to reach a 12 percent total metal loading. It is then calcined at 330° C. for 2.5 hours. Then it is reduced under a hydrogen atmosphere at a temperature of 332° to 337° C. for 16 hours. Following the reduction step it is stabilized at 60° C. for 30 to 40 hours.

Examples of other useful reductive amination catalysts are the rhodium atom-containing catalysts of U.S. Pat. No. 4,322,530, the copper-rhenium catalysts of U.S. Pat. No. 4,206,149, the nickel-cobalt-iron catalysts of U.S. Pat. No. 3,766,184, the cobalt-nickel-copper-containing aluminum oxide or silicon dioxide support catalyst of U.S. Pat. No. 4,014,933 and the catalyst containing copper oxide or copper hydroxide, nickel oxide or nickel hydroxide, and, optionally, an oxide or a hydroxide of a Group IIA metal of U.S. Pat. No. 4,409,399—the pertinent parts of such patents are incorporated herein by reference. U.S. Pat. No. 4,209,424 (the pertinent parts of which are incorporated herein by reference) teaches an amination catalyst which has at least one active metal from the group of transition metals consisting of nickel, cobalt and copper, uniformly combined with a refractory microporous substance.

The pertinent parts of U.S. Pat. No. 4,568,746 are incorporated herein by reference. The patent discloses a process for the production of an amine composition having a high ratio of diethylenetriamine to piperazine which comprises maintaining ethylenediamine in the presence of a nickel, cobalt or rhodium catalyst, wherein the metal is present on the surface of the catalyst in a polyatomic form, and at a temperature between about 170° to about 210° C. sufficient to convert less than about 35 percent of the ethylenediamine feed. The catalyst of U.S. Pat. No. 4,568,746 are nickel, cobalt or rhodium catalysts which can be relatively pure metal catalysts or catalysts that have been modified by the addition of molybdenum, chromium, iron or other transition metals in varying amounts. The catalysts can be in a massive form or they can be supported on a carrier such as the preferred silica or alumina carriers wherein the metal is present on the surface of the catalyst in a polyatomic form. Preferred catalysts are Raney nickel or Raney cobalt or a Ni/Re/B on silica catalyst prepared as described in U.S. Pat. No. 4,123,462. The catalyst charge, as a weight percent of the total charge, is not narrowly critical, although a charge of about 10 weight percent is preferred.

The pertinent portions of U.S. Pat. No. 4,625,030 are incorporated herein by reference. This patent discloses the potentiated nickel reductive amination catalysts discussed above.

The conditions of the reaction are not narrowly limited. As pointed out above, the reaction temperature and pressure is to be kept within about the ranges set forth above. The invention is not limited to a confining set of conditions. The reactants can be fed as a stream, typically continuously, to the bed of the catalyst. The catalyst is usually a fixed bed of solid particles (pellets, tablets, extrudates, spheres, etc.) which comprise the catalyst deposited on a solid, relatively inert support, such as those described above. The reaction occurs in the bed and thus the bed defines the reaction zone. The effluent from the bed or the reaction zone is also a stream comprising the unreacted components of the feed stream and the the principal reaction products EDA, DETA and AEEA, plus a number of other amine compounds. The TETAs and TEPAs comprise the various isomeric triethylenetetramines and tetraethylenepentamines.

The following examples are intended for the purpose of illustrating this invention and not for the purpose of limiting it.

EXAMPLES

The reactor used in the examples was a 74.75 inch-long Type 316 stainless steel medium pressure tube of 0.688 inch i.d. and 1.0 inch o.d. The temperature in the reaction zone was measured by three thermocouples evenly distributed in the reaction zone and placed in a ¼ inch o.d. thermowell located in the center of the tube. Two hundred grams of catalyst containing 6.1 wt. % nickel, 4.5 wt. % rhenium and 1.9 wt. % boron were charged to said reactor and held therein on a stainless steel screen at about 4 inches from the bottom of the tube. The free volume remaining in the tube was filled with an inert material of similar size to the catalyst.

Heating was supplied through the wall of the tube (when necessary) by three individually controlled heat tapes.

The process was operated according to the conditions set forth in the tables below for each of the enumerated examples. Ammonia was pumped to the system as liquid ammonia and mixed with hydrogen gas. This mixture was then passed through a preheater and mixed with MEA and EDA both of which had also been pumped to the system and passed through a preheater. This mixture then passed through another preheater prior to entering the reaction zone.

The reaction mixture was passed through the reaction zone in a downflow fashion. The pressure in the reaction zone was controlled by a motor valve at the outlet of the reactor. After leaving the reaction zone the pressure of the stream was reduced from that of the reaction zone to slightly above atmospheric. This stream was then passed through a dry ice/acetone trap where the hydrogen was separated from the condensables in the stream which were collected and ammonia removed in a semi-batch distillation leaving a mixture containing unreacted MEA and the products of the reaction.

The mixture of unreacted MEA and products of the reaction were then analyzed for water by a Karl-Fisher procedure and for organics (amines) by capillary gas chromatography. The EDA selectivity and mole percent set forth in the tables below represent net generated EDA.

The conditions used in the examples and the results are set forth in the following tables:

TABLE A

|  | Example | | | | | |
| --- | --- | --- | --- | --- | --- | --- |
|  | 1 | 2 | 3 | 4 | 5 | 6 |
| MEA conversion, % | 25 | 30 | 35 | 40 | 50 | 60 |
| pressure, psig | 2200 | 2200 | 2200 | 2200 | 2200 | 2200 |
| $NH_3$/MEA mole ratio | 7 | 7 | 7 | 7 | 7 | 7 |
| $H_2$ conc., mole % | 4.52 | 4.52 | 4.52 | 4.52 | 4.52 | 4.52 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 37.28 | 35.90 | 34.20 | 32.25 | 27.81 | 22.89 |
| MeEDA selectivity, % | 0.14 | 0.17 | 0.19 | 0.23 | 0.30 | 0.36 |
| PIP selectivity, % | 9.30 | 11.53 | 13.86 | 16.24 | 21.04 | 25.73 |
| EtEDA selectivity, % | 0.02 | 0.02 | 0.02 | 0.03 | 0.03 | 0.04 |
| DETA selectivity, % | 37.66 | 35.92 | 34.55 | 33.41 | 31.53 | 29.94 |
| AEEA selectivity, % | 10.88 | 11.10 | 11.01 | 10.71 | 9.63 | 8.15 |
| AEP selectivity, % | 1.26 | 1.53 | 1.87 | 2.29 | 3.42 | 4.88 |
| HEP selectivity, % | 0.11 | 0.13 | 0.15 | 0.17 | 0.24 | 0.34 |
| TETA selectivity, % | 2.73 | 3.00 | 3.32 | 3.70 | 4.63 | 5.74 |
| TEPA selectivity, % | 0.62 | 0.71 | 0.83 | 0.97 | 1.37 | 1.93 |
| product EDA, mole % | 54.98 | 53.58 | 51.81 | 49.73 | 44.72 | 38.71 |
| product DETA, mole % | 27.77 | 26.81 | 26.17 | 25.76 | 25.36 | 25.32 |
| product AEEA, mole % | 8.02 | 8.28 | 8.340 | 8.26 | 7.75 | 6.89 |
| product PIP, mole % | 6.85 | 8.61 | 15.50 | 12.52 | 16.92 | 21.75 |
| product MeEDA, mole % | 0.11 | 0.12 | 0.15 | 0.17 | 0.24 | 0.30 |
| product EtEDA, mole % | 0.01 | 0.01 | 0.02 | 0.02 | 0.03 | 0.04 |
| product AEP, mole % | 0.62 | 0.76 | 0.94 | 1.18 | 1.83 | 2.75 |
| product HEP, mole % | 0.05 | 0.06 | 0.07 | 0.09 | 0.13 | 0.19 |
| product TETA, mole % | 1.34 | 1.49 | 1.68 | 1.90 | 2.48 | 3.24 |
| product TEPA, mole % | 0.23 | 0.26 | 0.31 | 0.37 | 0.55 | 0.81 |

TABLE B

|  | Example | | | | | |
| --- | --- | --- | --- | --- | --- | --- |
|  | 7 | 8 | 9 | 10 | 11 | 12 |
| MEA conversion, % | 25 | 30 | 35 | 40 | 50 | 60 |
| pressure, psig. | 2200 | 2200 | 2200 | 2200 | 2200 | 2200 |
| $NH_3$/MEA mole ratio | 10 | 10 | 10 | 10 | 10 | 10 |
| $H_2$ conc, mole % | 4.52 | 4.52 | 4.52 | 4.52 | 4.52 | 4.52 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 40.82 | 40.10 | 38.93 | 37.41 | 33.58 | 28.98 |
| DETA selectivity, % | 36.09 | 34.50 | 33.24 | 32.19 | 30.49 | 29.03 |
| AEEA selectivity, % | 8.27 | 8.85 | 9.06 | 9.00 | 8.30 | 7.08 |
| PIP selectivity, % | 10.94 | 12.10 | 13.60 | 15.34 | 19.27 | 23.47 |
| MeEDA selectivity, % | 0.12 | 0.14 | 0.17 | 0.20 | 0.27 | 0.34 |
| EtEDA selectivity, % | 0.01 | 0.01 | 0.02 | 0.02 | 0.03 | 0.04 |
| AEP selectivity, % | 1.01 | 1.24 | 1.53 | 1.89 | 2.89 | 4.26 |
| HEP selectivity, % | 0.09 | 0.11 | 0.13 | 0.15 | 0.22 | 0.31 |
| TETA selectivity, % | 2.13 | 2.36 | 2.64 | 2.98 | 3.81 | 4.84 |
| TEPA selectivity, % | 0.50 | 0.58 | 0.68 | 0.81 | 1.15 | 1.64 |
| product EDA, mole % | 58.53 | 57.88 | 56.77 | 55.29 | 51.38 | 46.37 |
| product DETA, mole % | 25.87 | 24.90 | 24.23 | 23.79 | 23.33 | 23.22 |
| product AEEA, mole % | 5.93 | 6.39 | 6.61 | 6.65 | 6.35 | 5.66 |
| product PIP, mole % | 7.85 | 8.73 | 9.92 | 11.34 | 14.75 | 18.77 |
| product MeEDA, mole % | 0.09 | 0.10 | 0.12 | 0.15 | 0.20 | 0.27 |
| product EtEDA, mole % | 0.01 | 0.01 | 0.01 | 0.01 | 0.02 | 0.03 |
| product AEP, mole % | 0.48 | 0.59 | 0.74 | 1.93 | 1.48 | 2.27 |
| product HEP, mole % | 0.05 | 0.05 | 0.06 | 0.08 | 0.11 | 0.17 |
| product TETA, mole % | 1.02 | 1.14 | 1.28 | 1.47 | 1.94 | 2.58 |
| product TEPA, mole % | 0.18 | 0.21 | 0.25 | 0.30 | 0.44 | 0.66 |

TABLE C

| | Example | | | | | |
|---|---|---|---|---|---|---|
| | 13 | 14 | 15 | 16 | 17 | 18 |
| MEA conversion, % | 25 | 30 | 35 | 40 | 50 | 60 |
| pressure, psig | 2200 | 2200 | 2200 | 2200 | 2200 | 2200 |
| $NH_3$/MEA mole ratio | 10 | 10 | 10 | 10 | 10 | 10 |
| $H_2$ conc, mole % | 9.03 | 9.03 | 9.03 | 9.03 | 9.03 | 9.03 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 35.76 | 35.52 | 34.71 | 33.47 | 30.03 | 25.74 |
| DETA selectivity, % | 37.02 | 35.20 | 33.76 | 32.55 | 30.58 | 28.89 |
| AEEA selectivity, % | 11.04 | 11.29 | 11.22 | 10.93 | 9.85 | 8.34 |
| PIP selectivity, % | 11.22 | 12.35 | 13.81 | 15.52 | 19.33 | 23.36 |
| MeEDA selectivity, % | 0.11 | 0.13 | 0.15 | 0.18 | 0.24 | 0.31 |
| EtEDA selectivity, % | 0.01 | 0.01 | 0.02 | 0.02 | 0.03 | 0.04 |
| AEP selectivity, % | 1.12 | 1.37 | 1.68 | 2.07 | 3.12 | 4.52 |
| HEP selectivity, % | 0.12 | 0.14 | 0.16 | 0.19 | 0.26 | 0.37 |
| TETA selectivity, % | 2.76 | 3.03 | 3.37 | 3.76 | 4.72 | 5.86 |
| TEPA selectivity, % | 0.83 | 0.96 | 1.12 | 1.32 | 1.84 | 2.57 |
| product EDA, mole % | 53.37 | 53.21 | 52.43 | 51.17 | 47.51 | 42.60 |
| product DETA, mole % | 27.62 | 26.36 | 25.49 | 24.89 | 24.19 | 23.90 |
| product AEEA, mole % | 8.24 | 8.45 | 8.47 | 8.36 | 7.79 | 6.90 |
| product PIP, mole % | 8.38 | 9.25 | 10.43 | 11.86 | 15.29 | 19.32 |
| product MeEDA, mole % | 0.08 | 0.10 | 0.12 | 0.14 | 0.19 | 0.26 |
| product EtEDA, mole % | 0.01 | 0.01 | 0.01 | 0.02 | 0.02 | 0.03 |
| product AEP, mole % | 0.56 | 0.68 | 0.85 | 1.05 | 1.64 | 2.49 |
| product HEP, mole % | 0.06 | 0.07 | 0.08 | 0.10 | 0.14 | 0.21 |
| product TETA, mole % | 1.37 | 1.51 | 1.69 | 1.92 | 2.49 | 3.23 |
| product TEPA, mole % | 0.31 | 0.36 | 0.42 | 0.50 | 0.73 | 1.06 |

TABLE D

| | Example | | | | | |
|---|---|---|---|---|---|---|
| | 19 | 20 | 21 | 22 | 23 | 24 |
| conversion, % | 25 | 30 | 35 | 40 | 50 | 60 |
| pressure, psig | 2200 | 2200 | 2200 | 2200 | 2200 | 2200 |
| $NH_3$/MEA mole ratio | 4 | 4 | 4 | 4 | 4 | 4 |
| $H_2$ conc, mole % | 4.52 | 4.52 | 4.52 | 4.52 | 4.52 | 4.52 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 28.83 | 27.41 | 25.67 | 23.71 | 19.33 | 14.61 |
| DETA selectivity, % | 40.22 | 38.13 | 36.49 | 35.14 | 32.93 | 31.11 |
| AEEA selectivity, % | 15.34 | 14.91 | 14.31 | 13.58 | 11.87 | 9.94 |
| PIP selectivity, % | 9.30 | 12.50 | 15.53 | 18.44 | 23.88 | 28.86 |
| MeEDA selectivity, % | 0.17 | 0.20 | 0.23 | 0.26 | 0.33 | 0.38 |
| EtEDA selectivity, % | 0.02 | 0.03 | 0.03 | 0.03 | 0.04 | 0.05 |
| AEP selectivity, % | 1.62 | 1.93 | 2.32 | 2.81 | 4.06 | 5.58 |
| HEP selectivity, % | 0.13 | 0.15 | 0.17 | 0.20 | 0.27 | 0.38 |
| TETA selectivity, % | 3.59 | 3.87 | 4.23 | 4.65 | 5.66 | 6.81 |
| TEPA selectivity, % | 0.78 | 0.89 | 1.02 | 1.19 | 1.64 | 2.27 |
| product EDA, mole % | 45.53 | 43.86 | 41.77 | 39.33 | 33.56 | 26.75 |
| product DETA, mole % | 31.75 | 30.51 | 29.69 | 29.14 | 28.59 | 28.48 |
| product AEEA, mole % | 12.11 | 11.93 | 11.64 | 11.27 | 10.30 | 9.10 |
| product PIP, mole % | 7.34 | 10.00 | 12.64 | 15.29 | 20.73 | 26.43 |
| product MeEDA, mole % | 0.14 | 0.16 | 0.19 | 0.22 | 0.28 | 0.35 |
| product EtEDA, mole % | 0.02 | 0.02 | 0.02 | 0.03 | 0.04 | 0.05 |
| product AEP, mole % | 0.85 | 1.03 | 1.26 | 1.55 | 2.35 | 3.41 |
| product HEP, mole % | 0.07 | 0.08 | 0.09 | 0.11 | 0.16 | 0.23 |
| product TETA, mole % | 1.89 | 2.06 | 2.29 | 2.57 | 3.27 | 4.16 |
| product TEPA, mole % | 0.31 | 0.35 | 0.42 | 0.49 | 0.71 | 1.04 |

TABLE E

| | Example | | | | | |
|---|---|---|---|---|---|---|
| | 25 | 26 | 27 | 28 | 29 | 30 |
| MEA conversion, % | 25 | 30 | 35 | 40 | 50 | 60 |
| pressure, psig | 2200 | 2200 | 2200 | 2200 | 2200 | 2200 |
| $NH_3$/MEA mole ratio | 2 | 2 | 2 | 2 | 2 | 2 |
| $H_2$ conc, mole % | 4.52 | 4.52 | 4.52 | 4.52 | 4.52 | 4.52 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 19.90 | 18.94 | 17.57 | 15.90 | 12.04 | 7.80 |
| DETA selectivity, % | 42.61 | 40.12 | 38.19 | 36.61 | 34.08 | 32.04 |

TABLE E-continued

| | \multicolumn{6}{c}{Example} | | | | | |
|---|---|---|---|---|---|---|
| | 25 | 26 | 27 | 28 | 29 | 30 |
| AEEA selectivity, % | 19.60 | 18.48 | 17.36 | 16.22 | 13.89 | 11.55 |
| PIP selectivity, % | 10.31 | 14.08 | 17.51 | 20.68 | 26.40 | 31.47 |
| MeEDA selectivity, % | 0.20 | 0.23 | 0.26 | 0.29 | 0.35 | 0.40 |
| EtEDA selectivity, % | 0.03 | 0.03 | 0.04 | 0.04 | 0.05 | 0.06 |
| AEP selectivity, % | 1.93 | 2.27 | 2.71 | 3.24 | 4.56 | 6.10 |
| HEP selectivity, % | 0.15 | 0.16 | 0.19 | 0.22 | 0.30 | 0.41 |
| TETA selectivity, % | 4.35 | 4.63 | 5.00 | 5.44 | 6.47 | 7.63 |
| TEPA selectivity, % | 0.93 | 1.04 | 1.19 | 1.37 | 1.86 | 2.55 |
| product EDA, mole % | 33.93 | 32.64 | 30.73 | 28.34 | 22.43 | 15.32 |
| product DETA, mole % | 36.33 | 34.57 | 33.40 | 32.61 | 31.75 | 31.47 |
| product AEEA, mole % | 16.71 | 15.93 | 15.18 | 14.44 | 12.94 | 11.34 |
| product PIP, mole % | 8.79 | 12.13 | 15.31 | 18.42 | 24.60 | 30.91 |
| product MeEDA, mole % | 0.17 | 0.20 | 0.22 | 0.26 | 0.33 | 0.40 |
| product EtEDA, mole % | 0.02 | 0.03 | 0.03 | 0.04 | 0.05 | 0.06 |
| product AEP, mole % | 1.10 | 1.31 | 1.58 | 1.92 | 2.83 | 4.00 |
| product HEP, mole % | 0.08 | 0.09 | 0.11 | 0.13 | 0.18 | 0.27 |
| product TETA, mole % | 2.47 | 2.66 | 2.91 | 3.23 | 4.02 | 4.99 |
| product TEPA, mole % | 0.39 | 0.45 | 0.52 | 0.61 | 0.87 | 1.25 |

TABLE F

| | Example | | | | | |
|---|---|---|---|---|---|---|
| | 31 | 32 | 33 | 34 | 35 | 36 |
| MEA conversion, % | 25 | 30 | 35 | 40 | 50 | 60 |
| pressure, psig | 2200 | 2200 | 2200 | 2200 | 2200 | 2200 |
| $NH_3$/MEA mole ratio | 15 | 15 | 15 | 15 | 15 | 15 |
| $H_2$ conc, mole % | 4.52 | 4.52 | 4.52 | 4.52 | 4.52 | 4.52 |
| EDA/MEA mole ratio | 0.3611 | 0.3611 | 0.3611 | 0.3611 | 0.3611 | 0.3611 |
| MEA SV, gmol/hr/kg cat. | 12.44 | 12.44 | 12.44 | 12.44 | 12.44 | 12.44 |
| EDA SV, gmol/hr/kg cat. | 4.49 | 4.49 | 4.49 | 4.49 | 4.49 | 4.49 |
| temperature, °C. | 168.9 | 171.5 | 174.0 | 176.6 | 181.7 | 186.8 |
| EDA selectivity, % | 36.80 | 38.30 | 38.92 | 38.87 | 37.28 | 34.22 |
| DETA selectivity, % | 35.38 | 33.69 | 32.35 | 31.25 | 29.51 | 28.08 |
| AEEA selectivity, % | 7.44 | 8.21 | 8.58 | 8.65 | 8.13 | 7.00 |
| PIP selectivity, % | 17.62 | 16.60 | 16.39 | 16.77 | 18.73 | 21.70 |
| MeEDA selectivity, % | 0.09 | 0.11 | 0.14 | 0.16 | 0.23 | 0.31 |
| EtEDA selectivity, % | 0.01 | 0.01 | 0.01 | 0.01 | 0.02 | 0.03 |
| AEP selectivity, % | 0.73 | 0.90 | 1.13 | 1.42 | 2.23 | 3.44 |
| HEP selectivity, % | 0.08 | 0.09 | 0.11 | 0.13 | 0.19 | 0.27 |
| TETA selectivity, % | 1.47 | 1.65 | 1.87 | 2.13 | 2.79 | 3.66 |
| TEPA selectivity, % | 0.37 | 0.43 | 0.51 | 0.61 | 0.88 | 1.29 |
| product EDA, mole % | 54.18 | 55.83 | 56.56 | 56.61 | 55.19 | 52.20 |
| product DETA, mole % | 26.04 | 24.55 | 23.50 | 22.75 | 21.84 | 21.41 |
| product AEEA, mole % | 5.48 | 5.99 | 6.24 | 6.30 | 6.02 | 5.34 |
| product PIP, mole % | 12.97 | 12.10 | 11.91 | 12.21 | 13.87 | 16.55 |
| product MeEDA, mole % | 0.07 | 0.08 | 0.10 | 0.12 | 0.17 | 0.23 |
| product EtEDA, mole % | 0.01 | 0.01 | 0.01 | 0.01 | 0.01 | 0.02 |
| product AEP, mole % | 0.36 | 0.44 | 0.55 | 0.69 | 1.10 | 1.75 |
| product HEP, mole % | 0.04 | 0.04 | 0.05 | 0.06 | 0.09 | 0.14 |
| product TETA, mole % | 0.72 | 0.80 | 0.90 | 1.03 | 1.38 | 1.86 |
| product TEPA, mole % | 0.14 | 0.16 | 0.19 | 0.22 | 0.33 | 0.49 |

We claim:

1. A process of manufacturing an alkyleneamines reaction product mixture without a net increase in piperazine in the reaction product mixture comprising, based on 100% of the moles of the mixture and exclusive of any MEA and water present,
   a. about 20 to about 40 mole % DETA,
   b. about 15 to about 60 mole % EDA (net generated),
   c. about 5 to about 18 mole % AEEA,
   d. about 3 to about 25 mole % of the combination of PIP, AEP and HEP,
   e. less than about 1 mole to about 5 mole % of one or more of TETAs and TEPAs,
   f. less than about 1 mole % of other polyalkylene polyamines,
   g. a DETA and AEEA mole ratio greater than about 1.35, and
   h. an EDA to DETA mole ratio less than 2.60, which comprises feeding hydrogen, ammonia, MEA and a recycle stream comprising water, PIP and EDA to a reaction zone containing a fixed bed of a reductive amination catalyst in a tubular reactor, wherein the hydrogen comprises about 1 to about 30 mole percent of the feed in the reaction zone, the mole ratio of EDA to MEA is greater than 0.25 and the mole ratio of ammonia to MEA is about 1 to about 15, the temperature of the reaction zone is about 120° C. to about 300° C., the pressure of the reaction zone is about 1800 to about 2500 psig, the conversion of MEA is about 20 to about 60 weight percent, and recovering said alkyleneamines reaction product mixture from the reaction zone.

2. The process of claim 1 wherein the reductive amination catalyst contains nickel.

3. The process of claim 2 wherein the reductive amination catalyst contains rhenium.

* * * * *